US012564554B2

(12) United States Patent
Löbmann et al.

(10) Patent No.: US 12,564,554 B2
(45) Date of Patent: Mar. 3, 2026

(54) CO-AMORPHOUS FORMS OF BETA-LACTOGLOBULIN AND A DRUG SUBSTANCE

(71) Applicant: DISPERSOME IP APS, Copenhagen Ø (DK)

(72) Inventors: Korbinian Löbmann, Copenhagen N (DK); Donglei Leng, Søborg (DK); Ole Wiborg, Birkerød (DK)

(73) Assignee: DISPERSOME IP APS, Copenhagen Ø (DK)

( * ) Notice: Subject to any disclaimer, the term of this patent is extended or adjusted under 35 U.S.C. 154(b) by 475 days.

(21) Appl. No.: 17/779,566

(22) PCT Filed: Dec. 4, 2020

(86) PCT No.: PCT/EP2020/084754
§ 371 (c)(1),
(2) Date: May 25, 2022

(87) PCT Pub. No.: WO2021/110983
PCT Pub. Date: Jun. 10, 2021

(65) Prior Publication Data
US 2023/0009276 A1 Jan. 12, 2023

(30) Foreign Application Priority Data
Dec. 5, 2019 (EP) .................................... 19213832

(51) Int. Cl.
*A61K 9/14* (2006.01)
*A61K 9/16* (2006.01)

(52) U.S. Cl.
CPC ............ *A61K 9/146* (2013.01); *A61K 9/1658* (2013.01)

(58) Field of Classification Search
None
See application file for complete search history.

(56) References Cited

U.S. PATENT DOCUMENTS 8,791,064 B2 * 7/2014 Livney .................... A23L 33/15
977/773
2012/0093657 A1 4/2012 Kallesoe et al.
2016/0024339 A1 1/2016 Squiller et al.
2018/0362801 A1 12/2018 Wade et al.

FOREIGN PATENT DOCUMENTS

| CN | 109836980 A | 6/2019 |
|----|-------------|--------|
| CN | 110099696 A | 8/2019 |
| GB | 2560972 A | 10/2018 |
| JP | 2008-510779 A | 4/2008 |
| WO | WO 2006/021768 A1 | 3/2006 |
| WO | 2016210237 A1 | 12/2016 |

| WO | 2018113890 A1 | 6/2018 | |
|----|---------------|--------|---|
| WO | 2018115520 A1 | 6/2018 | |
| WO | WO-2018113890 | * 6/2018 | ............. A61K 47/34 |

OTHER PUBLICATIONS

Thomas et al. "Study of lactose/β-lactoglobulin interactions during storage" 2005.*
Stojadinovic et al. "One-step method for isolation and purification of native β-lactoglobluin from bovine whey" 2012.*
Sharma et al. "Preparation and Characterization of Solid Dispersions of Carvedilol with Poloxamer 188" 2013.*
Thomas et al. "Study of lactose/ β-lactoglobulin interactions during storage", Dairy Science and Technology (Le Lait), vol. 85, No. 4-5, Jul. 1, 2005, pp. 325-333.
Le Maux et al. "[beta]-Lactoglobulin-linoleate complexes; In vitro digestion and the role of protein in fatty acid uptake", Journal of Dairy Science, vol. 96, No. 7, Jul. 1, 2013, pp. 4258-4268.
Hancock et al. "What is the true solubility advantage for amorphous pharmaceuticals?", Pharmaceutical Research 17 (2000), pp. 397-404.
Laitinen et al. "Emerging trends in the stabilization of amorphous drugs", International Journal of Pharmaceutics vol. 453, issue 1 (2013), pp. 65-79.
Albrecht et al. "Addition of β-Lactoglobulin Produces Water-Soluble Shikonin", Journal of Agricultural & Food Chemistry, 2012, pp. 10834-10843.
Ipar, Vinod S. et al., "Enhancing Curcumin Oral Bioavailability Through Nanoformulations" European Journal of Drug Metabolism and Pharmacokinetics, 2019, pp. 459-480, vol. 44.
Truzzi, Francesca et al., "An Overview on Dietary Polyphenols and Their Biopharmaceutical Classification System (BCS)" International Journal of Molecular Sciences, 2021, pp. 1-23, vol. 22, No. 5514.
Leitlinie, Gemeinsame "S2k-Leitlinie Chronische Obstipation: Definition, Pathophysiologie, Diagnostik und Therapie" Feb. 2013, XP055854688.
Thomas, Marie E.C. "Influence de L'activite de L'eau Sur Les Interactions Lactose / β-Lactoglobuline de Poudres Laitiers Modeles Lyophilisees" Oct. 2004, XP055854730.
European Search Report for EP 24178410 dated Aug. 28, 2024.
Ruprichová, Lenka et al., "Determination of whey proteins in different types of milk" Acta Vet. Brno, 2014, pp. 67-72, vol. 83.
Office Action in JP 2022-534246 issued on Oct. 8, 2024.
Aditya, N.P. et al., "Fabrication of amorphous curcumin nanosuspensions using β-lactoglobulin to enhance solubility, stability, and bioavailability" Colloids and Surfaces B: Biointerfaces, 2015, pp. 114-121, vol. 127.
A Thesis Submitted in Partial Fulfillment of the Requirements for the Degree for the Master of Engineering "The Research of Nanocrystal about Oral Drugs Using Protein as Stabilizer", Candidate: Liu Lu, Huazhong University of Science & Technology, May 2016.
Office Action for CN 202080084595.7 issued Jan. 8, 2024.

* cited by examiner

*Primary Examiner* — Danah Al-Awadi
(74) *Attorney, Agent, or Firm* — KNOBBE, MARTENS, OLSON & BEAR, LLP

(57) ABSTRACT

The present invention relates to co-amorphous forms of a drug substance and a protein, more particularly beta-lactoglobulin, wherein the purity of the beta-lactoglobulin is at least 92% (w/w) of the total amount of protein comprised in the co-amorphous form. The present invention also relates to compositions, such as pharmaceutical compositions, comprising the co-amorphous form.

12 Claims, 12 Drawing Sheets

Dissolution of compound B-50% in 0.1M HCl

Dissolution of compound B-50% in FaSSIF-V2

Figure 8:
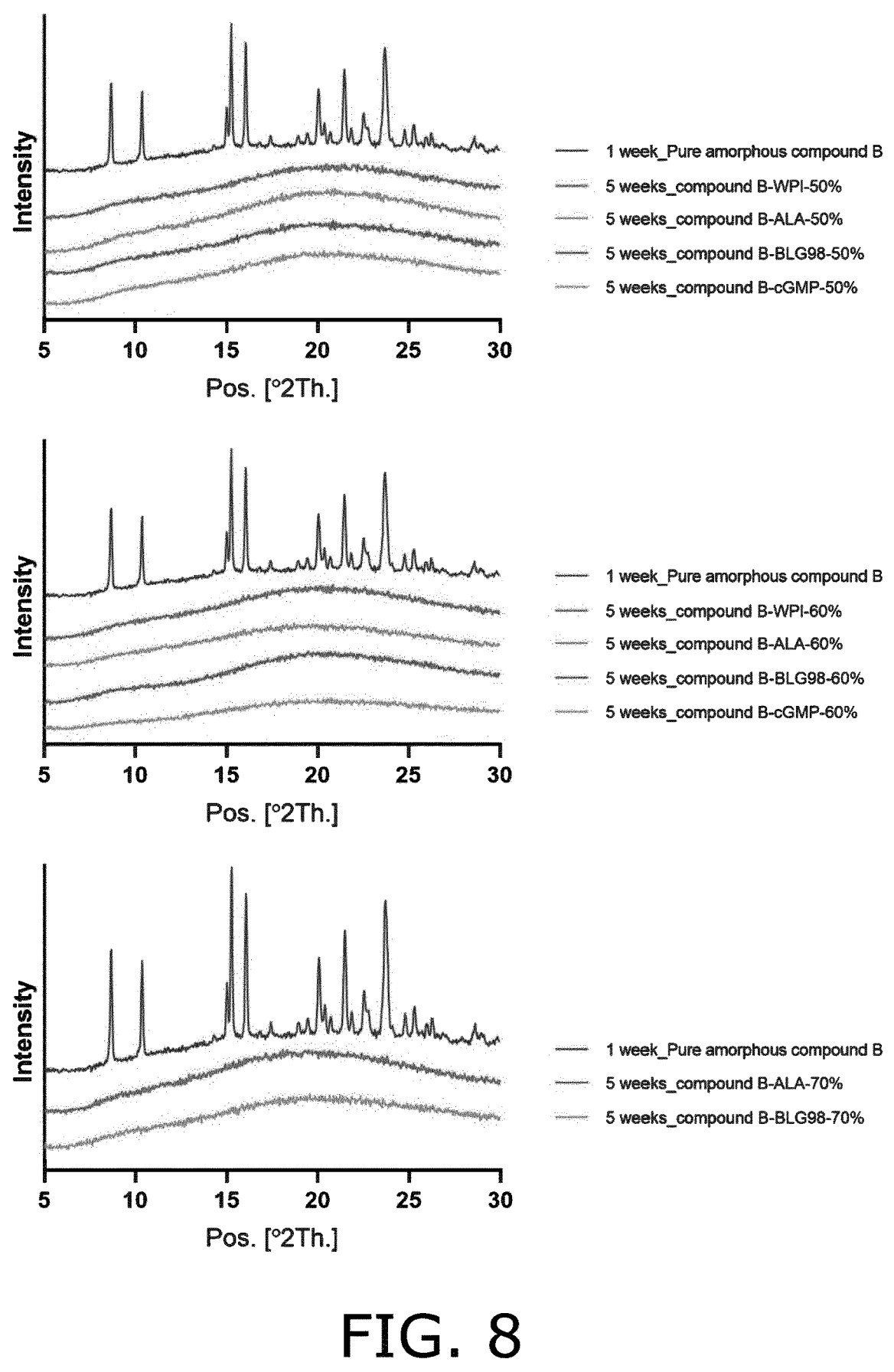

— 1 week_Pure amorphous compound B
— 5 weeks_compound B-WPI-50%
— 5 weeks_compound B-ALA-50%
— 5 weeks_compound B-BLG98-50%
— 5 weeks_compound B-cGMP-50%

— 1 week_Pure amorphous compound B
— 5 weeks_compound B-WPI-60%
— 5 weeks_compound B-ALA-60%
— 5 weeks_compound B-BLG98-60%
— 5 weeks_compound B-cGMP-60%

— 1 week_Pure amorphous compound B
— 5 weeks_compound B-ALA-70%
— 5 weeks_compound B-BLG98-70%

CO-AMORPHOUS FORMS OF BETA-LACTOGLOBULIN AND A DRUG SUBSTANCE

FIELD OF THE INVENTION

The present invention relates to co-amorphous forms of a drug substance and a protein, more particularly beta-lacto-globulin. The present invention also relates to compositions, such as pharmaceutical, cosmetic, veterinary, food or dietary compositions, comprising the co-amorphous form.

BACKGROUND OF THE INVENTION

Oral delivery is the preferred way of drug administration, since oral formulations are cheap to produce and convenient for the patient. However, oral formulation of crystalline drug substances with poor aqueous solubility is a major challenge for the pharmaceutical industry, since these substances exhibit poor solubility and low dissolution rates, resulting in low bioavailability and poor therapeutic performance.

Amorphous formulations have previously been used for addressing these issues. By converting the crystalline form of a drug into its amorphous counterpart, the solubility and dissolution rate of the drug substance is increased, leading to improved bioavailability and therapeutic efficacy (Hancock et al., Pharm. Res. 17 (2000) pp. 397-404). However, amorphous drug forms are physically unstable and tend to re-crystallize back into the poorly soluble crystalline form during storage (Laitinen et al., Int. J. Pharm. 453 (2013) pp. 65-79). Thus, methods for stabilizing amorphous drug forms are warranted by the pharmaceutical industry. Notably, there is a need in the art for new excipients that can further improve the stability and/or solubility properties of co-amorphous formulations.

Albreht et al. (J. Agric. Food Chem., 2012, 60, 10834-10843) disclose increasing solubility of shikonins using beta-lactoglobulin. The purity of the beta-lactoglobulin used in these experiments was 90%. Furthermore, Albreht et al. did not mention co-amorphous forms of the shikonins with beta-lactoglobulin.

WO 2018/113890 discloses co-amorphous forms of drug substances and various proteins. One of these proteins is beta-lactoglobulin. However, the purity of the beta-lacto-globulin is not specified, and the beta-lactoglobulin used in the examples was from bovine milk with a standard purity of around 90% (from Sigma-Aldrich, Germany). Further-more, with respect to dissolution enhancement using intrin-sic dissolution testing and amorphous physical stability, the highest performing proteins were found to be protein mix-tures and in particular whey protein isolate (WPI), which contains approximately 50 to approximately 70% beta-lactoglobulin.

In WO 2018/113890, intrinsic dissolution was used as it is a frequently used dissolution assessment technique, which minimizes the contribution of particle size effects or dis-persing effects in the dissolution medium. Without being bound by a particular theory, intrinsic dissolution does provide a general insight into the potential performance, but may not necessarily reflect the true dissolution behavior of a formulation or compound. Often, the dissolved amounts in an intrinsic dissolution experiment are so small, that they remain far below the saturation concentration of the drug in the dissolution medium (sink conditions). Hence, they pro-vide no information on the possibility of supersaturation or precipitation inhibition of a formulation. These properties can be assessed using powder dissolution that allows the formulations to supersaturate (non-sink conditions).

It has now surprisingly been found that beta-lactoglobulin with a higher purity performs better with respect to powder dissolution and physical stability than both WPI and beta-lactoglobulin having the standard purity.

Beta-lactoglobulin having higher purity than the standard purity may be prepared according to WO 2018/115520.

SUMMARY OF THE INVENTION

In one aspect, the present invention concerns a co-amor-phous form of a drug substance and beta-lactoglobulin, wherein the purity of the beta-lactoglobulin is at least 92% (w/w) of the total amount of protein comprised in the co-amorphous form.

In a further aspect, the present invention concerns the use of a beta-lactoglobulin having a purity of at least 92% (w/w) for preparing a co-amorphous form with a drug substance.

In another aspect of the invention, it concerns a pharma-ceutical composition comprising a co-amorphous form according to the invention and at least one pharmaceutically acceptable carrier or excipient.

DETAILED DESCRIPTION OF THE INVENTION

Definitions

In the context of the present invention, the term "co-amorphous" refers to a combination of two or more com-ponents that form a homogeneous amorphous system where the components are intimately mixed on the molecular level. The "co-amorphous" samples can be prepared by melt and solvent-based approaches, such as spray drying, solvent evaporation, freeze drying, precipitation from supercritical fluids, melt quenching, hot melt extrusion, electrospinning, 2D printing, 3D printing, or by kinetic disordering pro-cesses, such as ball milling and cryo-milling. X-ray powder diffraction (XRPD), together with Differential Scanning calorimetry (DSC), can be used to identify whether the sample is "co-amorphous" after preparation, e.g. by mea-suring the absence of Bragg peaks and the appearance of a single glass transition temperature.

In the context of the present invention, the term "purity" in connection with the beta-lactoglobulin comprised in the co-amorphous form according to the invention is defined as a percentage (w/w) of the total amount of protein comprised in the co-amorphous form. When the co-amorphous form is comprised in a pharmaceutical composition, any additional protein, such as gelatin, that may be included as an excipient in the pharmaceutical formulation does not enter into the calculation of the purity of the beta-lactoglobulin comprised in the co-amorphous form. Furthermore, if an additional protein is included as an excipient in a pharmaceutical composition, said additional protein may give rise to an additional, second glass transition temperature (if amor-phous) or melting point (if crystalline) in addition to the glass transition temperature of the co-amorphous form.

In the context of the present invention, the term "drug substance" is intended to refer to an active pharmacetical ingredient, a nutraceutical, or a veterinary medicinal prod-uct. In one embodiment, the term "drug substance" refers to an active pharmaceutical ingredient. When referring to "a" drug substance in the context of the present invention, it may refer to one or more drug substances.

Co-Amorphous Forms

In one aspect, the present invention concerns a co-amorphous form of a drug substance and beta-lactoglobulin, wherein the purity of the beta-lactoglobulin is at least 92% (w/w) of the total amount of protein comprised in the co-amorphous form. Without being bound by a particular theory, it has been found that the purity of the beta-lactoglobulin contributes positively towards a higher solubility and/or stability of the drug substance. Accordingly, in one embodiment of the present invention, the the purity of the beta-lactoglobulin in the co-amorphous form of the invention is at least 94% (w/w) of the total amount of protein comprised in the co-amorphous form. In another embodiment of the present invention, the purity of the beta-lactoglobulin in the co-amorphous form of the invention is at least 95% (w/w) of the total amount of protein comprised in the co-amorphous form. In still another embodiment of the present invention, the purity of the beta-lactoglobulin in the co-amorphous form of the invention is at least 96% (w/w) of the total amount of protein comprised in the co-amorphous form. In yet another embodiment, the purity of the beta-lactoglobulin in the co-amorphous form of the invention is at least 97% (w/w) of the total amount of protein comprised in the co-amorphous form. In a further embodiment of the present invention, the purity of the beta-lactoglobulin in the co-amorphous form of the invention is at least 98% (w/w) of the total amount of protein comprised in the co-amorphous form.

The co-amorphous form of the invention may contain from 1 to 99% (w/w) of the drug substance, such as from 5 to 95% (w/w) of the drug substance. In one embodiment, the co-amorphous form comprises from 10 to 90% (w/w) of the drug substance and from 10 to 90% (w/w) of the beta-lactoglobulin. In a further embodiment, the co-amorphous form comprises from 20 to 90% (w/w) of the drug substance and from 10 to 80% (w/w) of the beta-lactoglobulin. In still a further embodiment, the co-amorphous form comprises from 30 to 85% (w/w) of the drug substance and from 15 to 70% (w/w) of the beta-lactoglobulin. In another embodiment, the co-amorphous form comprises from 50 to 85% (w/w) of the drug substance and from 15 to 50% (w/w) of the beta-lactoglobulin. In a further embodiment, the co-amorphous form comprises from 55 to 75% (w/w) of the drug substance and from 25 to 45% (w/w) of the beta-lactoglobulin. In yet another embodiment, the co-amorphous form comprises 30% (w/w) of the drug substance and 70% (w/w) of the beta-lactoglobulin. In yet a further embodiment, the co-amorphous form comprises 50% (w/w) of the drug substance and 50% (w/w) of the beta-lactoglobulin. In still a further embodiment, the co-amorphous form comprises 60% (w/w) of the drug substance and 40% (w/w) of the beta-lactoglobulin. In yet another embodiment, the co-amorphous form comprises 70% (w/w) of the drug substance and 30% (w/w) of the beta-lactoglobulin.

It has been found that lower drug loadings provide particularly good dissolution of drug molecules having low solubility, especially for drug molecules having very low solubility. Accordingly, in one embodiment, the co-amorphous form comprises from 5 to 35% (w/w) of the drug substance and from 65 to 95% (w/w) of the beta-lactoglobulin. In a further embodiment, the co-amorphous form comprises from 10 to 30% (w/w) of the drug substance and from 70 to 90% (w/w) of the beta-lactoglobulin. In still a further embodiment, the co-amorphous form comprises from 12 to 25% (w/w) of the drug substance and from 75 to 88% (w/w) of the beta-lactoglobulin. In yet a further embodiment, the co-amorphous form comprises from 15 to 20% (w/w) of the drug substance and from 80 to 85% (w/w) of the beta-lactoglobulin.

In a further aspect, the present invention concerns the use of a beta-lactoglobulin having a purity of at least 92% (w/w) for preparing a co-amorphous form with a drug substance.

The co-amorphous forms may be prepared according to the present examples or according to the general methods disclosed in WO 2018/113890. Accordingly, in one aspect, the present invention concerns a method of preparing a co-amorphous form of the invention, said method selected from subjecting the drug substance and beta-lactoglobulin together to spray drying, solvent evaporation, freeze drying, precipitation from supercritical fluids, melt quenching, hot melt extrusion, electrospinning, 2D printing, 3D printing, and any milling process, such as ball milling and cryo-milling.

Drug Substances

Most new pharmaceutically active molecules are very hydrophobic and thus difficult to dissolve in water. Examples of such molecules are those classified in classes II and IV of the Biopharmaceutics Classification System (BCS). Accordingly, these pharmaceutically active molecules are typically in need of solubilization in order to improve their bioavailability in the final formulation. Thus, in one embodiment, the present invention concerns a co-amorphous form of a drug substance and beta-lactoglobulin, wherein the purity of the beta-lactoglobulin is at least 92% (w/w) of the total amount of protein comprised in the co-amorphous form, and wherein the drug substance is classified in classes II or IV of the BCS. In a further embodiment, the crystalline drug substance has a solubility in water at 25° C. of less than 0.1 mg/ml. In still a further embodiment, the crystalline drug substance has a solubility in water at 25° C. of less than 0.02 mg/ml.

It is contemplated that the present concept is of a general character, i.e. it can be applied to all types of drug substances for which an improved amorphous physical stability and/or solubility is advantageous. Such drug substance may be classified as poorly or not soluble, poorly or not permeable, and/or slowly dissolving according to the biopharmaceutics classification system. Such drug substance may be selected from the following list: abiraterone acetate, aceclofenac, acetaminophen, acetazolamide, acetylsalicylic acid, aclidinium bromide, acyclovir, afamelanotide acetate, albendazole, albuterol sulfate, aliskiren fumarate, allopurinol, alprostadil, amantadine hydrochloride, aminolevulinic acid hydrochloride, amiodarone hydrochloride, amoxicillin, amprenavir, anagrelide hydrochloride, anidulafungin, apalutamide, apixaban, apremilast, aprepitant, apriprazole, atorvastatin, azelaic acid, azithromycin, benidipine, bazedoxifene acetate, bedaquiline fumarate, benzonatate, bexarotene, bicalutamide, binimetinib, bisacodyl, brivaracetam, budesonide, candesartan, carbamazepine, cabergoline, carfilzomib, carisoprodol, carvedilol, cefdinir, cefditoren, cefixime, cefotiam, cefpodoxime, cefuroxime axetil, celecoxib, chlarithromycin, chloroquine, chlorpromazine, ciclesonide, cilexetil, cilostazol, ciprofloxacin, cladribine, clarithromycin, clofazimine, clonazepam, clopidogrel, clozapine, cobicistat, colistimethate sodium, cyclosporine, cyproterone, dabrafenib mesylate, dapaglifozin, dapsone, daptomycin, dasabuvir, dasatinib, deferasirox, delafloxacin meglumine, dexamethasone, dexmethylphenidate hydrochloride, diazepam, diclofenac, diloxanide, docetaxel, dolutegravir sodium, doxycycline, dutasteride, duvelisib, ebastine, efavirenz, eluxadoline, elvitegravir, empagliflozin, enasidenib mesylate, enzalutamide, epalrestat, eprosartan, erythromycin, eslicarbazepine acetate, estradiol, estrone sulphate, ethyl icosapentate, etoposide, etravirine, everolimus, ezetimibe, famotidine, fenofibrate, flibanserin, fluocinonide, flurbiprofen, fluticasone furoate, fluticasone propionate, folic acid, formoterol fumarate, furosemide, gefitinib, glatiramer acetate, glibenclamide, gliclazide, glimpiride, glipizide, glycopyrrolate, griseofulvin, haloperidol, hydrochlorothiazide, hydrocortisone, hydroxyzine, ibuprofen, ibrutinib, icosapent ethyl, imatinib, indinavir, irbesartan, irinotecan, isotretinoin, itraconazole, ivacaftor, ivermectin, ketoprofen, L-carbocysteine, lamotrigine, lenalidomide, lesinurad, letermovir, levalbuterol tartrate, levodopa, levonorgestrel, linezolid, lopinavir, loratadine, lorazepam, lovastatin, lubiprostone, manidipine, mebendazole, medroxyprogesterone, mefloquine, megestrol acetate, melatonin, meloxicam, melphalan, menatetrenone, mercaptopurine, mesalamie, metaxalone, methylphenidate, metoclopramide, metoprolol, metronidazole, midostaurin, modafinil, mometasone furoate, morphine sulfate, mosapride, mycamine, nabilone, nabumetone, nalidixic acid, naproxen sodium, nelfinavir, nepafenac, nevirapine, neratinib, nicergoline, niclosamide, nifedipine, nilotinib, nilvadipine, nimesulide, nimodipine, nintedanib, nitisinone, nitrofurantoin, norethindrone acetate, nystatin, olanzapine, olaparib, olmesartan, omadacycline, opicapone, orlistat, ospemifene, oxcarbazepine, oxycodone, paclitaxel, paliperidone palmitate, palonosetron hydrochloride, paricalcitol, pazopanib hydrochloride, perampanel, phenobarbital, phenytoin, pioglitazone, pitavastatin, posaconazole, pranlukast, praziquantel, prednisolone acetate, prednisone, progesterone, pyrantel, pyrimethamine, quetiapine, quinine, raloxifene, rebamipide, regorafenib, retinol, ribociclib succinate, rifampicin, rifaximin, rilpivirine, rimegepant, riociguat, risperidone, ritonavir, rivaroxaban, rofecoxib, rolapitant hydrochloride, roxithromycin, rucaparib, safinamide mesylate, saquinavir, sennoside A, sertraline, sevelamer carbonate, sildenafil, simeprevir, simvastatin, sirolimus, sofosbuvir, sonidegib phosphate, sorafenib tosylate, spironolactone, sufentanil citrate, sugammadex sodium, sulfadiazine, sulfamethoxazole, sulfasalazine, sultamicillin, sulpiride, sunitinib malate, suvorexant, tacrolimus, tadalafil, tafamidis, tafamidis meglumine, tamoxifen, tasimelteon, tecovirimat, telaprevir, telmisartan, telotristat ethyl, teprenone, teriflunomide, theophylline, ticlopidine, tipranavir, tocopherol nicotinate, tolterodine tartrate, topotecan hydrochloride, tosufloxacin, tretinoin, triflusal, trimethoprim, umeclidinium bromide, uridine triacetate, ursodeoxycholic acid, valproic acid, valsartan, vandetanib, vemurafenib, venetoclax, verapamil, voriconazole, warfarin, ziprasidone hydrochloride and zaltoprofen.

Some drug substances contain functional groups that are alkaline and thus give rise to salts with acids. Other drug substances contain functional groups that are acidic and thus give rise to salts with bases. Typically, drug substances containing one or more acidic functional groups will maintain their low solubility in gastric acid since they are not prone to protonation in the gastric acid. On the other hand, drug substances containing one or more alkaline groups will increase their solubility in gastric acid due to protonation. It has been found that the advantages obtained with the co-amorphous forms of the invention are not limited by the presence or absence of acidic and alkaline groups and the invention is therefore envisioned to be useful for all types of drug substances.

Beta-Lactoglobulin

Beta-lactoglobulin is the major whey protein in the milk of ruminants and many other mammals. Whey refers to the liquid supernatant that is left after the casein of milk has been precipitated and removed (during cheese production). However, beta-lactoglobulin may also be isolated directly from milk. Bovine beta-lactoglobulin is a protein of 162 amino acids, having a molecular weight of approximately 18.4 kDa. Under physiological conditions, the protein is predominantly dimeric (in an open form) while it dissociates to the monomeric state (closed conformation) at pH below 3. The pH is also important for the crystallization of bovine beta-lactoglobulin that may form different lattices depending on the pH. Several genetic variants of beta-lactoglobulin have been identified, the main bovine ones termed A and B. In one embodiment of the present invention, beta-lactoglobulin is beta-lactoglobulin obtained from mammalian species, such as cow, sheep or goat, in its native and/or glycosylated form and includes the genetic variants. It is contemplated as part of the present invention that also modifications including additions, deletions, substitutions of amino acids in the protein of the naturally occurring forms and variants thereof, or recombinant forms of beta-lactoglobulin are useful in the present invention. In a further embodiment, the beta-lactoglobulin is bovine beta-lactoglobulin.

Pharmaceutical Compositions

The co-amorphous forms of the invention may be included in a pharmaceutical composition. Hence, in one aspect of the invention, it concerns a pharmaceutical composition comprising a co-amorphous form according to the invention and at least one pharmaceutically acceptable carrier or excipient.

The co-amorphous forms of the invention are preferably formulated with a pharmaceutically acceptable carrier or excipient. A pharmaceutically acceptable carrier or excipient is an inert carrier or excipient suitable for each administration method and can be formulated into conventional pharmaceutical preparation (tablets, granules, capsules, powder, solution, suspension, emulsion, injection, infusion, etc.). As such a carrier or excipient there may be mentioned, for example, a binder, a lubricant, a disintegrant and the like, which are pharmaceutically acceptable. When they are used as an injection suspension or an infusion suspension, they can be formulated by using distilled water for injection, physiological saline, an aqueous glucose solution.

The administration method of the pharmaceutical compositions of the present invention is not particularly limited, and a usual oral or parenteral administration method (intravenous, intramuscular, subcutaneous, percutaneous, intranasal, transmucosal, enteral, etc.) can be applied. In one embodiment, the pharmaceutical composition is in a form suitable for oral or nasal administration, such as a solid formulation, powder, tablets, capsule, granules, sachets, reconstitutable powders, powders, dry powder inhalers and chewables.

It should be understood that any feature and/or aspect discussed above in connections with the compounds according to the invention apply by analogy to the methods described herein.

The following figures and examples are provided below to illustrate the present invention. They are intended to be illustrative and are not to be construed as limiting in any way.

Figure 1:
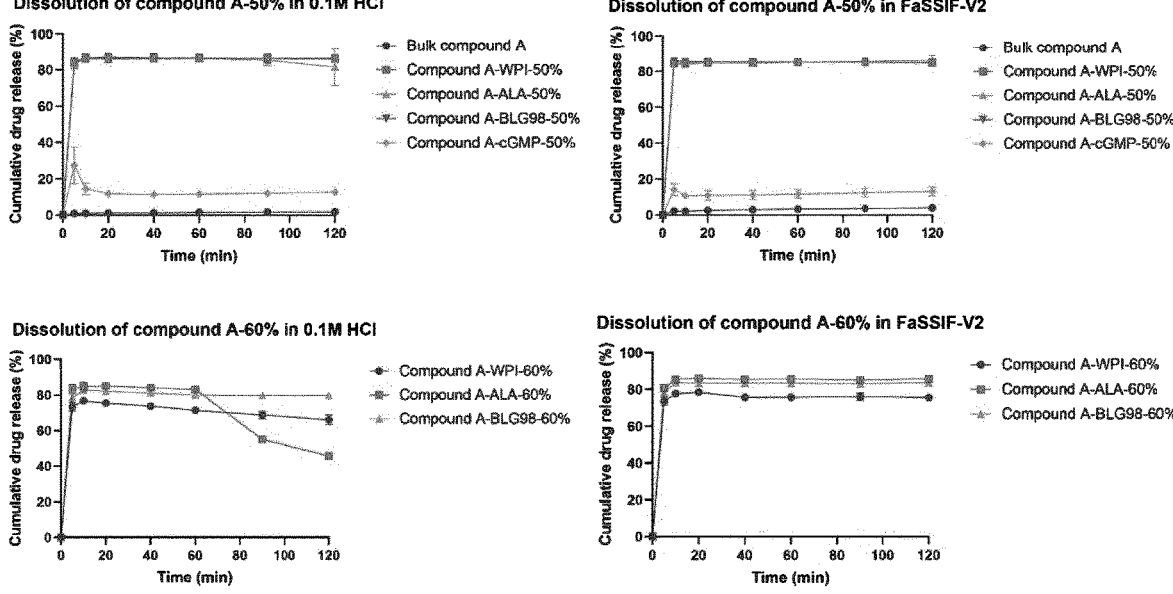
FIG. 1

Powder dissolution of crystalline Compound A as well as co-amorphous formulations at 50% (WPI, ALA, BLG98 and cGMP) and 60% (WPI, ALA and BLG98) drug loadings in 0.1M HCl and FaSSIF-V2.

FIG. 2

Powder dissolution of crystalline Compound B as well as co-amorphous formulations at 50% (WPI, ALA, BLG98 and cGMP), 60% (WPI, ALA, BLG98 and cGMP) and 70% (ALA and BLG98) drug loadings in 0.1M HCl and FaSSIF-V2.

FIG. 3

Powder dissolution of co-amorphous formulations at 50% (BLG98 and BLG90, respectively) Compound B drug loadings in 0.1M HCl and FaSSIF-V2.

FIG. 4

Powder dissolution of co-amorphous formulations at 50% (WPI, BLG98 and BLG90, respectively) indomethacin drug loadings in 0.1M HCl and FaSSIF-V2.

FIG. 5

XRPD diffractograms of the freshly milled pure drug Compound A as well as the co-amorphous formulations at 50%, 60% and 70% (w/w) drug loading in combination with the proteins WPI, ALA, BLG98, cGMP.

FIG. 6

XRPD diffractograms of the freshly milled pure drug Compound B as well as the co-amorphous formulations at 50% and 60% (w/w) drug loading in combination with the proteins WPI, ALA, BLG98, cGMP. At 70% (w/w) drug loading, co-amorphous were only prepared with ALA and BLG98.

FIG. 7

XRPD diffractograms of the stored samples of drug Compound A. The shown diffractograms indicate whether the samples remained amorphous (5 weeks halo) or the appearance of crystalline peaks at the first occurrence during the stability study (indicated by the week number).

FIG. 8

XRPD diffractograms of the stored samples of drug Compound B. The pure amorphous drug showed crystallinity already after 1 week of storage, whereas all investigated co-amorphous formulations at 50%, 60% and 70% (w/w) drug loading show the amorphous halo.

FIG. 9

XRPD diffractograms of the stored samples (40° C./75% RH) of the drug indomethacin in co-amorphous formulation with WPI, BLG90 and BLG98 at 50% drug loading, respectively. The shown diffractograms indicate whether the samples remained amorphous (1 month halo) or in case of BLG90 the appearance of crystalline peaks after 1 week during the stability study.

FIG. 10

XRPD diffractograms of the stored samples (ambient conditions) of the drug indomethacin in co-amorphous formulation with WPI, BLG90 and BLG98 at 50% drug loading, respectively. The shown diffractograms indicate whether the samples remained amorphous (1 month halo) or in case of BLG90 the appearance of crystalline peaks after 1 week during the stability study.

FIG. 11

XRPD diffractograms of various freshly milled co-amorphous formulations at 50% drug loading in combination with BLG98 and BLG90.

FIG. 12

Powder dissolutions of crystalline compounds APA, BDQ, RIF, RIT and VNX and the respective co-amorphous formulations at 50% drug loading in combination with BLG98 and BLG90 in 0.1M HCl and FaSSIF-V2.

FIG. 13

XRPD diffractograms of the freshly milled and stored co-amorphous formulations comprising Compound IND at 30% drug loading in combination with BLG98 and BLG90.

FIG. 14

Powder dissolutions of co-amorphous formulations of Compound IND at 30% drug loading in combination with BLG98 and BLG90 in 0.1M HCl and FaSSIF-V2. The co-amorphous formulations were obtained by ball milling.

FIG. 15

XRPD diffractograms of freshly spray dried co-amorphous formulations at 50% RIF drug loading in combination with BLG98 and BLG90.

FIG. 16

Powder dissolution of co-amorphous formulation at 50% RIF drug loading in combination with BLG98 and BLG90 in 0.1M HCl and FaSSIF-V2. The co-amorphous formulations were obtained by spray drying.

EXAMPLES

Materials

Drug Compound A and drug Compound B are small molecule active compounds. Compound A (melting point (Tm)=284° C., log P=1.8, pKa=6.3 (acid) and 9.8) has a solubility in water at 25° C. of 0.02 mg/ml, and a solubility at pH 1 at 25° C. of 0.02 mg/ml. Compound B (Tm=259° C., log P=2, neutral) has a solubility in water at 25° C. of 0.01 mg/ml and of 0.3 mg/ml at pH 1 (25° C.). Indomethacin (IND, Tm=162° C., log P=4.3, pKa=4.5 (acid)) was purchased from Hawkins, Inc. (Minneapolis, MN, USA). Whey protein isolate (WPI), beta-lactoglobulin with a purity of >98% in the protein fraction (BLG98), alpha-lactalbumin (ALA) and casein glycomacroprotein (cGMP) were obtained from Arla Food Ingredients. Beta-lactoglobulin with a purity of approx. 90% in the protein faction (BLG90) was obtained from Sigma-Aldrich.

Apalutamide (APA), bedaquiline fumarate (BDQ), nimodipine (NMD), rifaximin (RIF), ritonavir (RIT), and venetoclax (VNX) are small molecule active compounds with different physico-chemical properties comprising acidic, basic and neutral molecules as well as an ionic compound in form of a salt.

Methods

Ball Milling

Protein-based co-amorphous forms were prepared using vibrational ball milling (MixerMill MM400, Retsch GmbH & Co., Haan, Germany) in a 4° C. cold room for 60 min at 30 Hz. For this purpose, a total mass of 500 mg materials at the respective weight ratio between proteins and drug (30%, 50%, 60% or 70% drug loading) was weighed into 25 ml milling jar and milling was performed with two 12 mm stainless steel balls.

Spray Drying

Protein-based co-amorphous forms were prepared by using a Büchi B-290 spray dryer (Büchi Labortechnik AG, Falwil, Switzerland), equipped with a three-fluid nozzle (Büchi Labortechnik AG, Flawil, Switzerland), an inert loop B-295 (Büchi Labortechnik AG) and a dehumidifier (Büchi Labortechnik AG). Compound RIF was dissolved in ethanol (absolute, ≥99.8%) at a concentration of 20 mg/ml as the inner feed solution, BLG98 or BLG90 was dissolved in water at a concentration of 20 mg/ml and used as the outer feed solution. The inner feed solution and the outer feed solution were separately pumped into the spray dryer at a constant feeding rate of 1.8 ml/min. The spray drying process was conducted under the following process settings: inlet temperature of 100° C., drying air flow rate of ca. 35 m³/h and atomization air flow rate of 473 l/h. The outlet temperature was recorded to be 65-70° C.

X-Ray Powder Diffraction (XRPD) for Measurement of the Solid State Form

The presence of a fully amorphous formulation or one with crystallinity was measured using an X'Pert PANanalytical PRO X-ray diffractometer (PANanalytical, Almelo, The Netherlands) with Cu Kα radiation (λ=1.54187 Å). Samples were scanned in reflectance mode from 5° to 30° 2θ, with a scan speed of 0.067° 2θ/s and a step size of 0.026° 2θ. The acceleration voltage and current are 45 kV and 40 mA, respectively.

Powder Dissolution Testing in 0.1M HCl, FaSSGF and FaSSIF

The powder dissolution of the samples was determined at room temperature in either 0.1M HCl or fasted state simulated intestinal fluid V2 (FaSSIF V2, Biorelevant) as dissolution medium. Samples equivalent to 20 mg of drug were added into a 100 ml of Erlenmeyer flask containing 20 ml of dissolution medium. A magnetic stirring bar was added to the Erlenmeyer flask containing the dissolution medium and stirred at 200 rpm. At predetermined time points (5, 10, 20, 40, 60, 90, 120 min), 2 ml of dissolution medium were withdrawn from the dissolution vessels and immediately replaced by 2 ml of fresh dissolution medium. The dissolution samples were then filtered through a 0.45 μm filter and diluted using acetonitrile, and subsequently filtered again through a 0.45 μm filter. Finally, the samples were analyzed toward drug content using high performance liquid chromatography (HPLC) in case of Compound A, Compound B, Compound IND, Compound NMD, Compound RIF, Compound RIT and Compound VNX (with BLG90); or UV spectroscopy in case of Compound APA, Compound BDQ and Compound VNX (with BLG98). For HPLC analysis, an Agilent 1260 infinity HPLC system (Agilent, Santa Clara, USA) equipped with an Agilent 1290 Diode Array Detector was used. The column was an Agilent 5 TC-C18 (2) 250*4.6 mm, 5 μm and the injection volume was 20 μl. The flow rate was 1 ml/min for all compounds. A 5 TC-C18 (2) (Agilent, 4.6×150 mm, 5 μm) column was used for the quantifications of Compound A, Compound B, Compound RIF and Compound RIT. An Eclipse XDB-C18 (Agilent, 4.6×150 mm, 5 μm) column was used for the quantification of Compound VNX (with BLG90).

For Compound A, the mobile phase consisted of 15 mM ammonium dihydrogen phosphate in water and acetronitrile at a volume ratio of 3 to 7, whereas for Compound B, the mobile phase consisted of 0.05% TFA in water and acetronitrile at a volume ratio of 4 to 6. The UV detection wavelengths were 225 nm and 248 nm for Compound A and Compound B, respectively. The retention times were approx. 3.9 min and 4.3 min for Compound A and Compound B, respectively. For indomethacin, the mobile phase consisted of 1.25% phosphoric acid in water and methanol at a volume ratio of 15 to 85. The UV detection wavelength was 240 nm and the retention time was approx. 5.5 min.

For Compound RIF, the mobile phase was 20 volumes of 3.16 g/l ammonium formate (pH 7.2±0.05) and 80 volumes of a mixture of equal volumes of acetonitrile and methanol. The UV detection wavelength was 276 nm and the retention time was approx. 5.6 min. For Compound RIT, the mobile phase was a mixture of 2 g/l KH₂PO₄ in water and acetonitrile at a volume ratio of 45 to 55. The mobile phase was adjusted to pH of 4.0±0.05 by using H₃PO₄. The UV detection wavelength was 215 nm and the retention time was approx. 11.7 min. For Compound VNX (with BLG90), the mobile phase was 10 volumes of 25 mM ammonium formate (pH 6.5) and 90 volumes of acetonitrile. The UV detection wavelength was 250 nm and the retention time was approx. 5.3 min.

For Compound APA, BDQ, and VNX (with BLG98), the samples were analyzed by using an Evolution 300 UV spectrophotometer (Thermo Scientific, Cambridge, UK) at 320 nm.

Physical Stability

All samples containing Compound A and Compound B were stored in a desiccator at 40° C. over a saturated sodium chloride solution to obtain 75% relative humidity (40° C./75% RH). Samples containing Compound A, Compound B and IND [IND at a drug loading of 50% (w/w)] were tested towards their solid state by XRPD at day 0 and subsequently after 1, 3 and 5 weeks. Samples containing indomethacin were stored both at 40° C./75% RH and under ambient conditions and analyzed after 1 week and 1 month of storage. Samples containing IND at a drug loading of 30% (w/w) were tested towards their solid state by XRPD at day 0 and subsequently after 3 weeks.

Modulate Temperature Differential Scanning Calorimetry (mDSC) for Measurement of the Glass Transition Temperature (Tg) and Homogeneity of the Co-Amorphous Forms The mDSC thermograms of the samples were collected using a Discovery DSC (TA instruments, New Castle, USA) under a nitrogen gas flow of 50 ml/min. The samples containing Compound A, Compound B and IND were analysed at a heating rate of 2° C./min from 25° C. to 200° C., with an underlying modulation temperature amplitude of 0.2120° C. and a period of 40 s. For the remaining samples the same heating rate, amplitude and period were applied. Samples containing compounds APA, BDQ, RIF and VNX were heated from 25° C. to 250° C., and samples containing Compound RIT were heated from 0° C. to 170° C. A total of 4-8 mg sample powder was filled into aluminium Tzero pans and sealed with an aluminium Tzero lid. The glass transition temperature (Tg) was determined as the midpoint from the reversing heat flow signal.

Example 1—Powder Dissolution of the Co-Amorphous Formulations (Drugs Compound A, Compound B, and Indomethacin)

At a Compound A loading of 50% (w/w), the co-amorphous formulations containing WPI, ALA and BLG98 release approx. 90% of Compound A and perform equally in 0.1M HCl and FaSSIF (FIG. 1). At a Compound A loading of 60% (w/w), however, the co-amorphous formulations containing WPI, ALA and BLG98 perform differently. In the dissolution medium 0.1M HCl, the co-amorphous formulations with ALA and BLG98 release initially approx. 80% of Compound A (5 min to 60 min) and subsequently, the formulation containing ALA shows precipitation of the drug, whereas the formulation containing BLG98 remains at its concentration level and does not show any signs of precipitation. The co-amorphous formulation containing WPI reaches slightly lower concentration at approx. 75% Compound A release after 10 min and a slight but continuous decrease in concentration to approx. 70% Compound A release at 120 min. Hence it performs overall inferior to BLG98 (entire experiment) and ALA (first 60 min of the experiment). In the dissolution medium FaSSIF, the co-amorphous form with ALA and BLG98 perform equally, releasing quickly approx. 80% of Compound A, which remains at its concentration level and does not show any signs of precipitation. The co-amorphous formulation containing WPI reaches slightly lower concentrations at approx. 75% Compound A release and performs overall inferior to ALA and BLG98 (entire experiment). Lastly, all co-amorphous formulations (50 and 60% drug loading) perform better than the pure crystalline Compound A.

Figure 2:
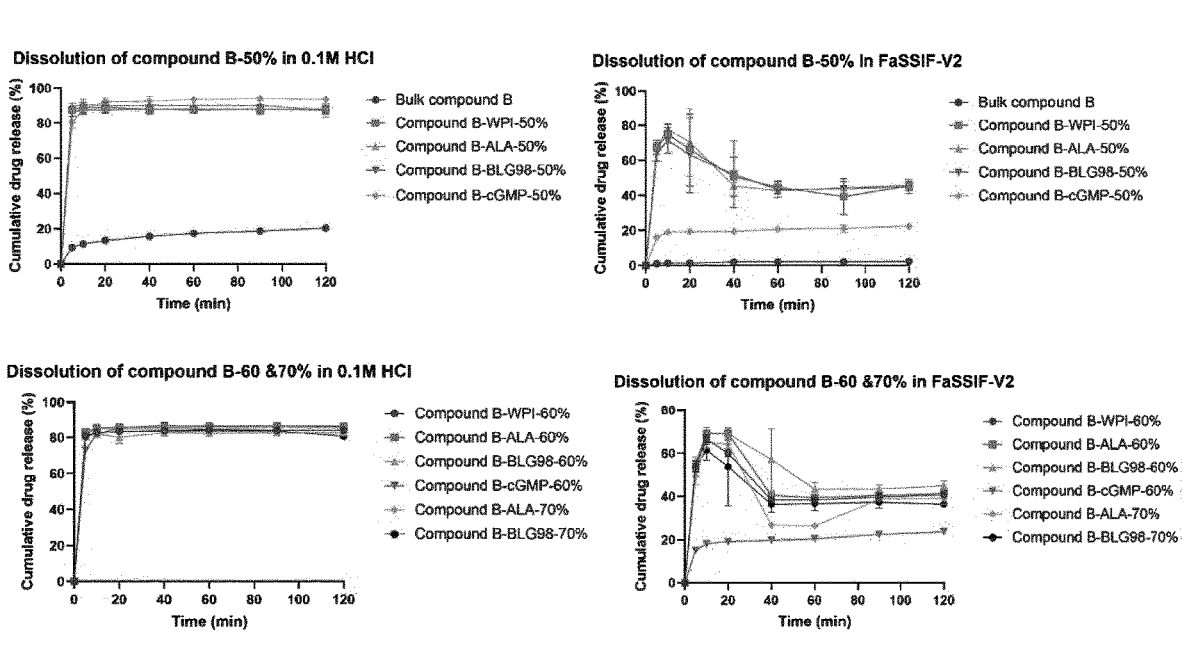

At a Compound B loading of 50% and 60% (w/w), the co-amorphous formulations containing WPI, ALA, BLG98 and cGMP release approx. 90% and 80% of Compound B, respectively, in 0.1 M HCl, which is kept until the end of the experiment (FIG. 2). Similarly, at a Compound B loading of 70% (w/w), the co-amorphous formulations containing ALA and BLG98 releases approx. 80% of Compound B in 0.1 M HCl, which is kept until the end of the experiment.

In FaSSIF, the co-amorphous formulations at a Compound B loading of 50% and 60% (w/w) containing WPI, ALA and BLG98 release initially approx. 70% of Compound B (10 min) followed by a precipitation of Compound B to concentration levels of approx. 40% drug release. The co-amorphous formulations at a Compound B loading of 70% (w/w) containing ALA and BLG98 show a similar performance. On the contrary, the co-amorphous formulation at a Compound B loading of 50% and 60% (w/w) containing cGMP performs inferior to all other formulations in FaSSIF, releasing a total of approx. 20% Compound B.

Lastly, all co-amorphous formulations (50, 60% and 70% drug loading) perform better than the pure crystalline Compound B.

Figure 3:
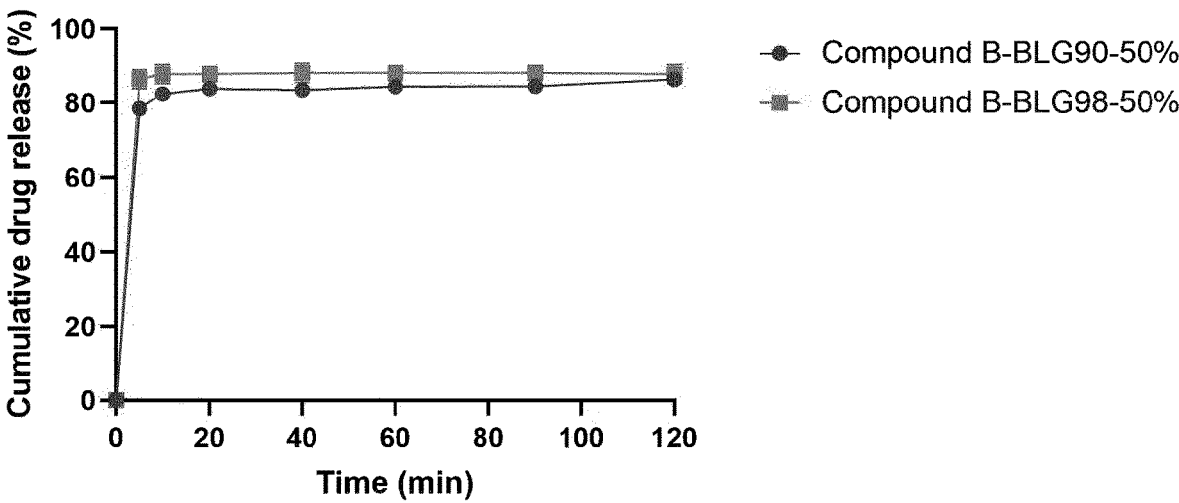
Figure 3:
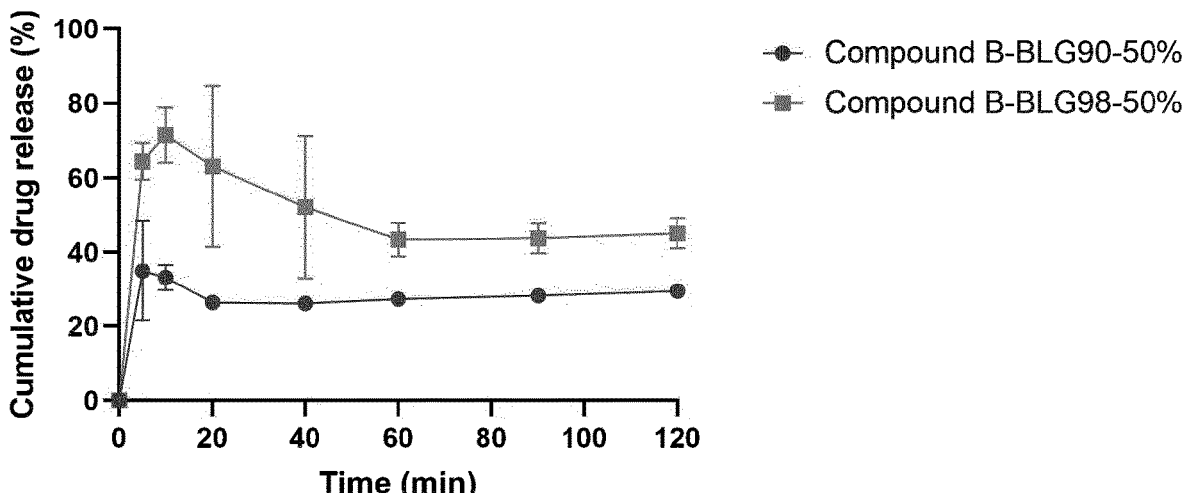

At a Compound B loading of 50% (w/w), the co-amorphous formulations containing BLG98 and BLG90 release approx. 85 and 80%, respectively, in 0.1M HCl. In FaSSIF V2, they release approx. 45 and 30%, respectively (FIG. 3). This demonstrates that the beta-lactoglobulin with the higher purity provides improved solubility and dissolution for Compound B in both acidic and neutral media.

Figure 4:
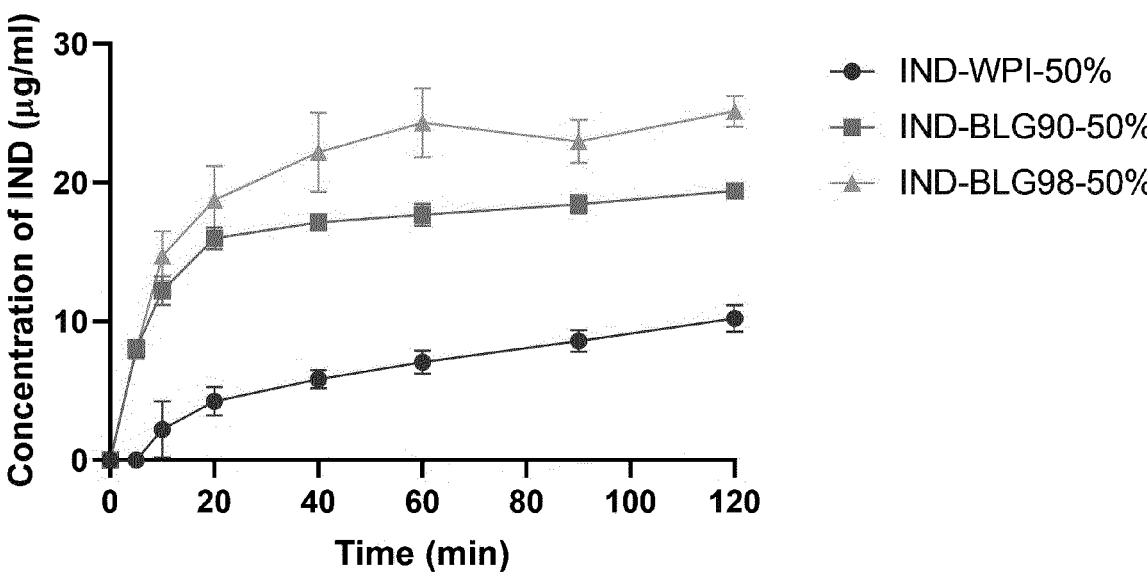
Figure 4:
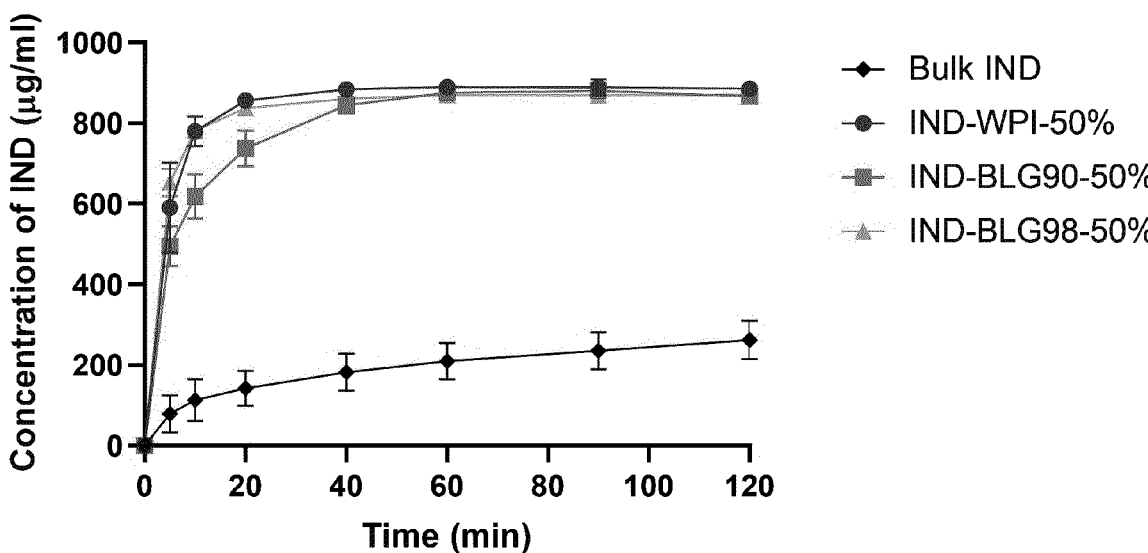

At an indomethacin loading of 50% (w/w), the co-amorphous formulations containing BLG98 demonstrated a higher release than both WPI and BLG90 in 0.1 M HCl, with BLG90 performing better than WPI (FIG. 4). In FaSSIF, the different protein grades showed similar final release profiles. However, BLG98 reached the plateau faster than BLG90 (FIG. 4).

Overall, considering the outcome of the dissolution study, the pure crystalline drugs perform inferior to any co-amorphous formulation. Within the co-amorphous formulations, cGMP performs inferior to WPI, ALA and BLG98. Considering the results for Compound A only, BLG98 appears to be superior compared to ALA and WPI at a drug loading of 60% (w/w) and equal at a drug loading of 50% (w/w). For Compound B, similar results for WPI, ALA and BLG98 were obtained with respect to the dissolution behavior. For Compound B and indomethacin, BLG98 was clearly superior to BLG90, and for indomethacin also with respect to WPI. Hence, the higher purity of beta-lactoglobulin provides improved properties compared to the 90% purity of the prior art forms.

Figure 5:
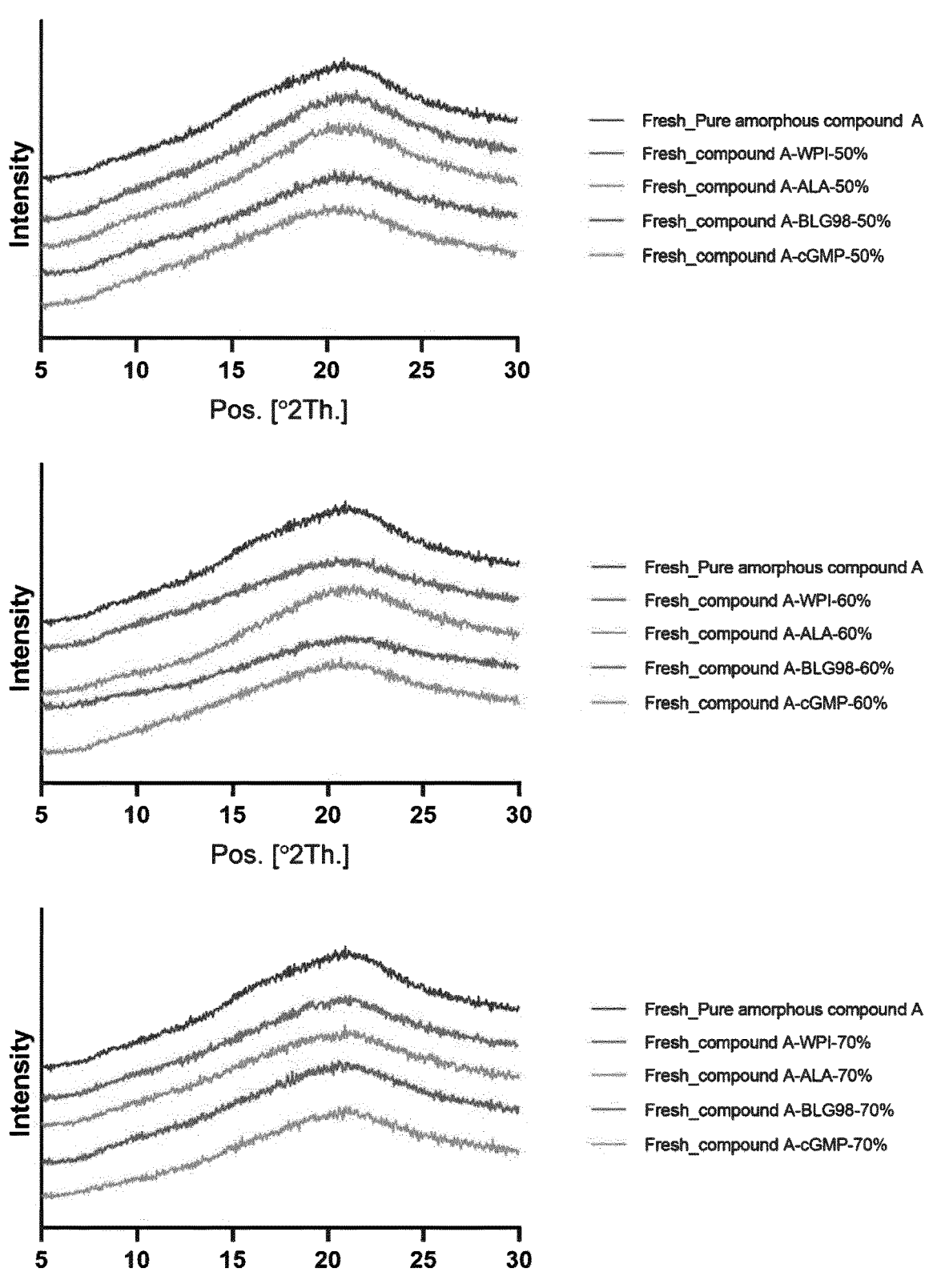
Figure 6:
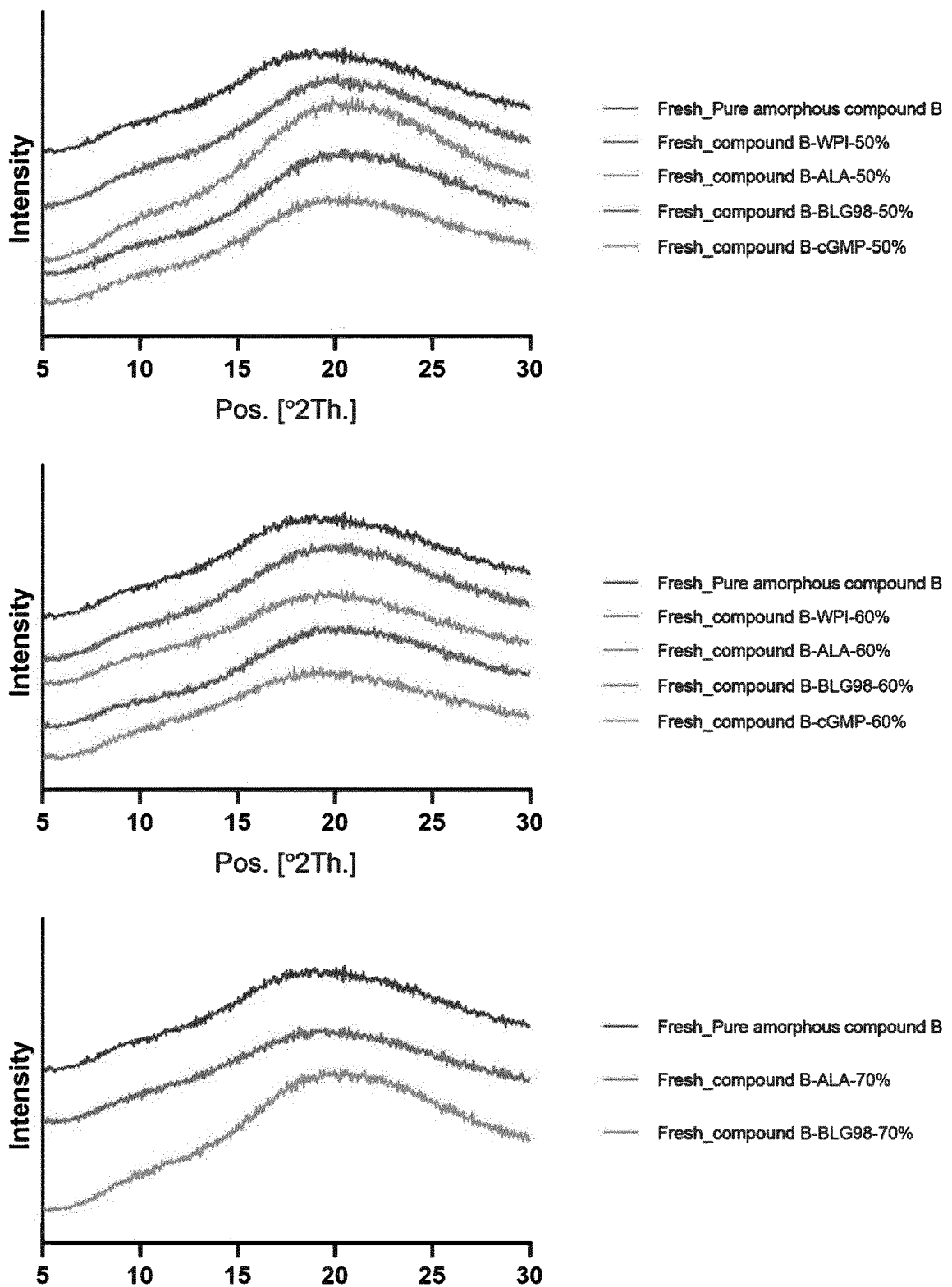

Example 2—Physical Stability of Co-Amorphous Samples Containing the Drugs Compound A, Compound B, and Indomethacin XRPD was used to analyze the solid state of the samples. An amorphous material is indicated by the appearance of an amorphous halo structure in the XRPD, i.e. no Bragg peaks in the diffractograms, whereas the presence of crystallinity can be identified by the presence of crystalline peaks in the diffractograms. FIGS. 5 and 6 show the appearance of the amorphous halo in each case, proving the success in amorphization either for the pure drugs Compound A and Compound B or for all drug-protein mixtures. Physical stability was performed under humid conditions at 40° C. and 75% RH in open vials.

Figure 7:
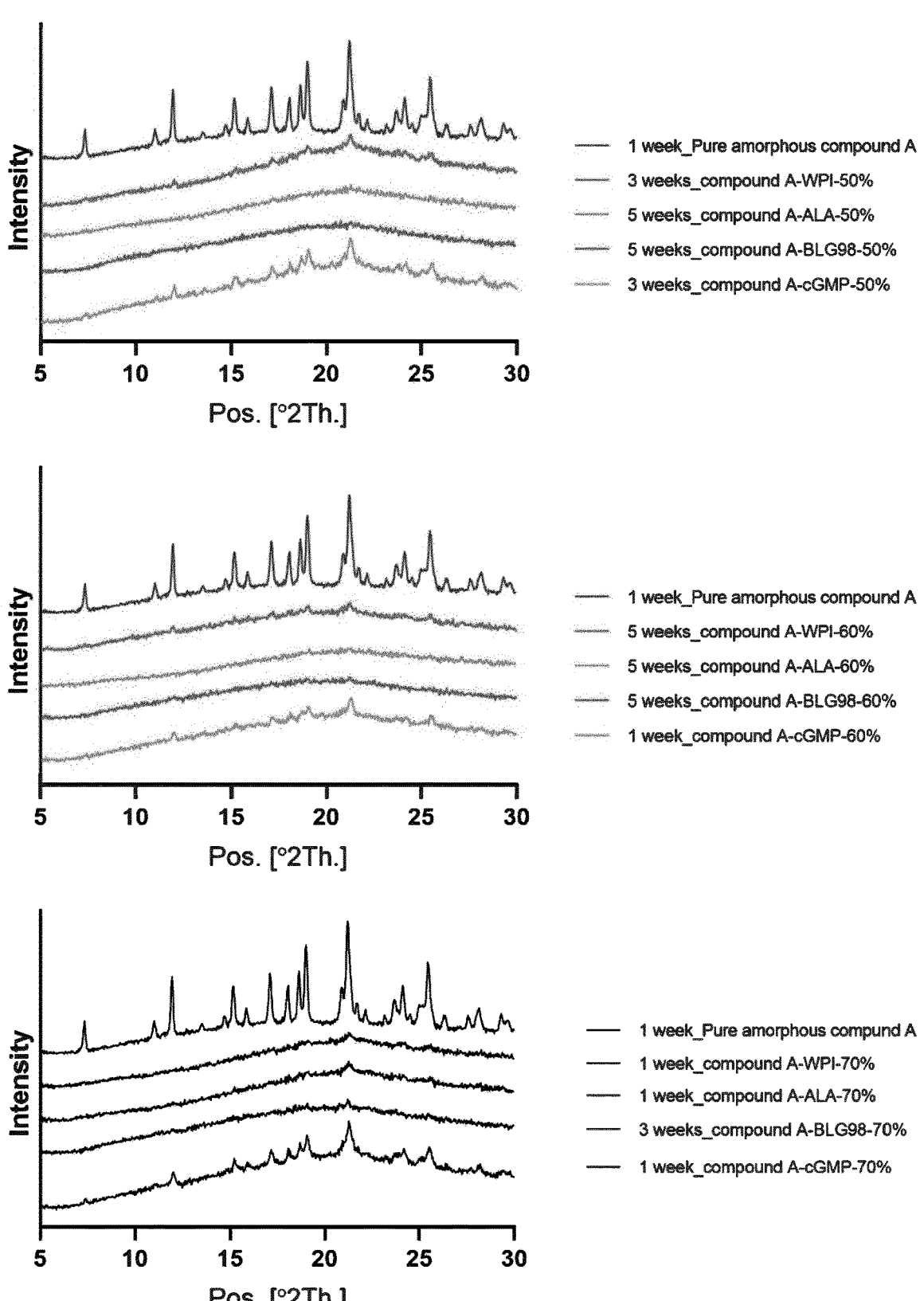

Upon storage, it can be seen that that the pure amorphous drugs Compound A and Compound B are unstable and show the appearance of crystalline peaks already within 1 week of storage (FIGS. 7 and 8). For Compound A at the drug loadings 50% and 60% (w/w), the co-amorphous formulations containing ALA and BLG98 remain amorphous for the entire duration (5 weeks) whereas the co-amorphous formulations containing WPI or cGMP show crystalline peaks after 1 week (Compound A-cGMP 60%), 3 weeks (Compound A-cGMP 50%, Compound A-WPI 50%) or 5 weeks (Compound A-WPI 60%) of storage (FIG. 7). For Compound A at the drug loading 70% (w/w), the co-amorphous formulations containing WPI, ALA and cGMP show crystalline peaks after 1 week, whereas BLG98 remains amorphous after 1 week, but shows crystalline peaks after 3 weeks. For Compound B at the drug loadings 50%, 60% and 70% (w/w), all investigated co-amorphous formulations remain amorphous for the entire duration (5 weeks) (FIG. 8).

Figure 9:
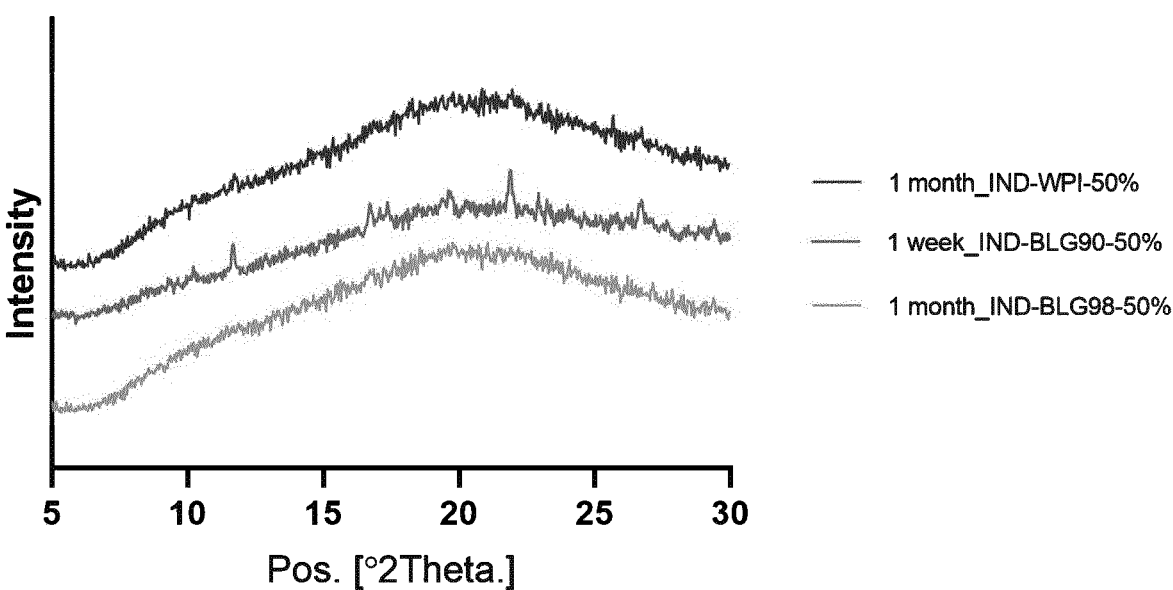
Figure 10:
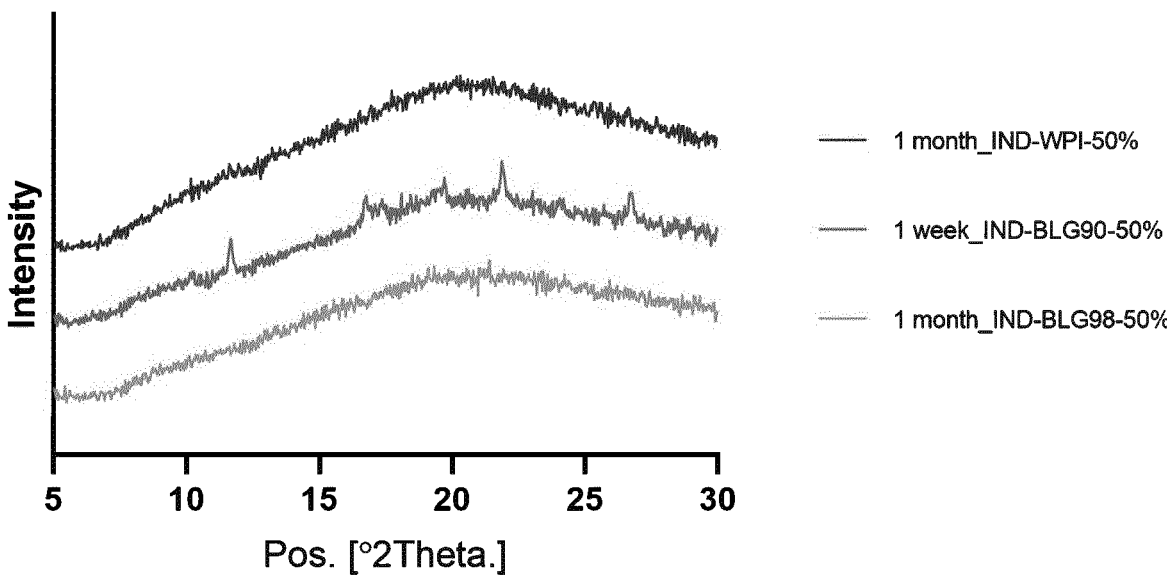

Indomethacin stored at accelerated conditions (40° C./75% RH) and at ambient conditions in co-amorphous formulation with WPI, BLG90 and BLG98, respectively, at 50% drug loading demonstrated that BLG98 has improved stability compared to BLG90 (FIGS. 9 and 10). After 1 month, BLG98 still has an amorphous halo, whereas BLG90 shows crystalline peaks after 1 week. WPI also maintains the amorphous form longer than BLG90.

Overall, considering the outcome of the stability study, the pure drugs require an amorphous stabilizer and comparatively BLG98 performed best.

Example 3—Thermal Analysis of the Co-Amorphous Formulations

Table 1 reveals that the Tg of the pure drugs Compound A and Compound B are both lower than for any of the co-amorphous formulations. The appearance of a single Tg in any of the mDSC thermograms of the co-amorphous formulations, suggest that all formulations resulted in homogeneous single phase amorphous systems of the in combination with all proteins, WPI, ALA, BLG98 and cGMP. It can furthermore be seen that all proteins, WPI, ALA, BLG98 and cGMP, result in Tgs with similar values for each respective drug loading. For those samples which remained amorphous after 5 weeks storage, the Tg was reanalyzed and it can be seen the Tg remains very similar to the freshly prepared Tg, indicating that storage did not change the homogeneity of these co-amorphous formulations.

TABLE 1 mDSC data on the Tg of the amorphous drugs Compound A and Compound B as well as the freshly prepared and stored co-amorphous formulations.

| Sample description | Tg_fresh (° C.) | Tg_5 weeks (° C.) |
|---|---|---|
| Pure amorphous 1001 | 114.2 | |
| Pure amorphous 1002 | 113.8 | |
| 1001-WPI-50% | 155.4 | — |
| 1001-ALA-50% | 155.3 | 157.4 |
| 1001-BLG98-50% | 155.6 | 153.0 |
| 1001-cGMP-50% | 160.7 | — |

TABLE 1-continued mDSC data on the Tg of the amorphous drugs Compound A and Compound B as well as the freshly prepared and stored co-amorphous formulations.

| Sample description | Tg_fresh (° C.) | Tg_5 weeks (° C.) |
|---|---|---|
| 1001-WPI-60% | 147.9 | — |
| 1001-ALA-60% | 150.9 | 149.2 |
| 1001-BLG98-60% | 150.0 | 149.8 |
| 1001-cGMP-60% | 157.0 | — |
| 1001-WPI-70% | 141.0 | — |
| 1001-ALA-70% | 143.7 | |
| 1001-BLG98-70% | 144.4 | 139.4 |
| 1001-cGMP-70% | 144.8 | — |
| 1002-WPI-50% | 123.0 | 120.1 |
| 1002-ALA-50% | 126.1 | 125.2 |
| 1002-BLG98-50% | 123.2 | 123.2 |
| 1002-cGMP-50% | 124.2 | 116.8 |
| 1002-WPI-60% | 119.9 | 122.0 |
| 1002-ALA-60% | 124.0 | 123.2 |
| 1002-BLG98-60% | 123.0 | 119.8 |
| 1002-cGMP-60% | 125.3 | 120.2 |
| 1002-ALA-70% | 126.7 | 119.3 |
| 1002-BLG98-70% | 118.4 | 118.3 |

Example 4—Preparation, Diffractometric Analysis, Thermal Analysis and Powder Dissolution of Co-Amorphous Formulations at 50% Drug Loading in Combination with BLG98 or BLG90 Obtained by Ball Milling (Drugs APA, BDQ, RIF, RIT and VNX)

Figure 11:
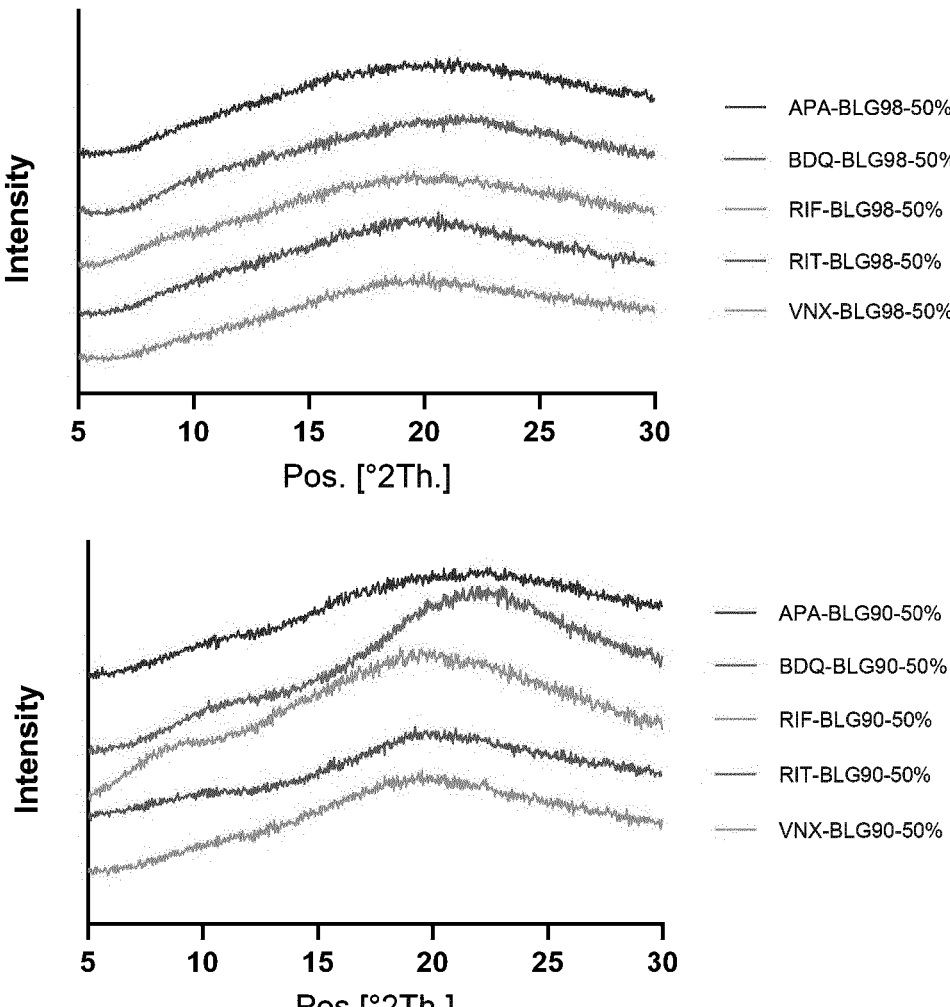

Freshly prepared co-amorphous formulations at a drug loading of 50% (w/w) showed the appearance of an amorphous halo (FIG. 11) as well as a single glass transition temperature (Table 2), suggesting that all formulations resulted in single phase amorphous systems in combination with either BLG98 or BLG90.

TABLE 2 mDSC data on the Tg of the pure amorphous drugs and the freshly prepared co-amorphous formulations.

| Sample description | Tg (° C.) |
|---|---|
| Pure amorphous APA | 97.4 |
| APA-BLG98-50% | 105.4 |
| APA-BLG90-50% | 102.1 |
| Pure amorphous BDQ | 79.4 |
| BDQ-BLG98-50% | 160.8 |
| BDQ-BLG90-50% | 161.1 |
| Pure amorphous RIF | 194.4 |
| RIF-BLG98-50% | 213.1 |
| RIF-BLG90-50% | 211.0 |
| Pure amorphous RIT | 41.7 |
| RIT-BLG98-50% | 46.0 |
| RIT-BLG90-50% | 46.0 |
| Pure amorphous VNX | 120.1 |
| VNX-BLG98-50% | 127.3 |
| VNX-BLG90-50% | 130.3 |

Figure 12:
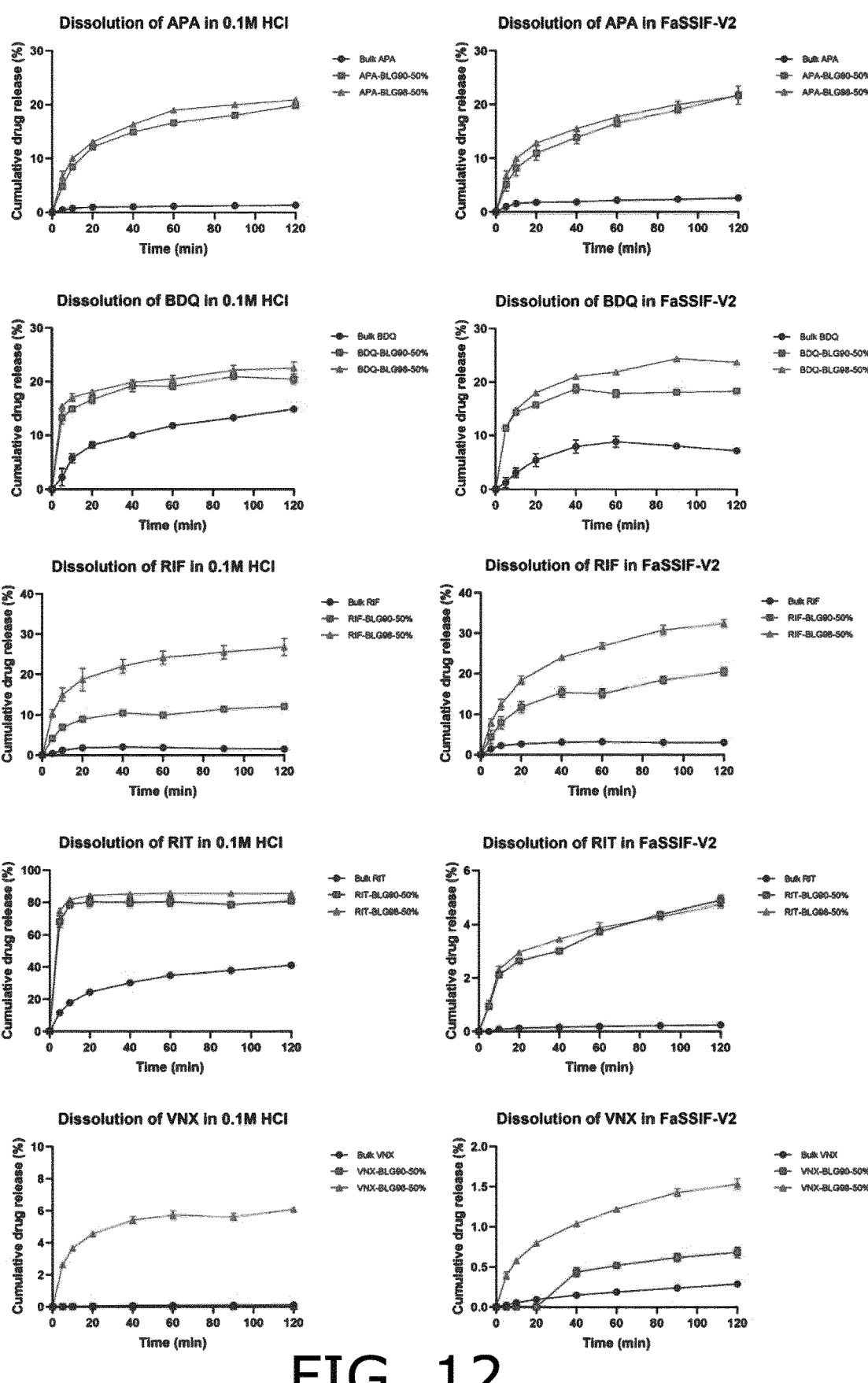

The co-amorphous formulations containing the compounds APA, BDQ, RIF, RIT and VNX together with BLG98 or BLG90, all at a drug loading of 50% (w/w), showed a substantial increase in dissolution rate and solubility in both dissolution media compared to the respective pure crystalline compounds (FIG. 12). Furthermore, it can be seen that the co-amorphous formulation prepared with BLG98 generally showed a faster dissolution and higher solubility compared to the respective co-amorphous formulation prepared with BLG90.

Overall, BLG98 provides improved dissolution and solubility for various compounds with different physico-chemical properties at a drug loading of 50% (w/w) compared to the respective crystalline drugs and co-amorphous formulation prepared with BLG90.

Example 5-Preparation, Physical Stability, Thermal Analysis and Powder Dissolution of Co-Amorphous Formulations at 30% Drug Loading in Combination with BLG98 Obtained by Ball Milling (Drug IND)

Figure 13:
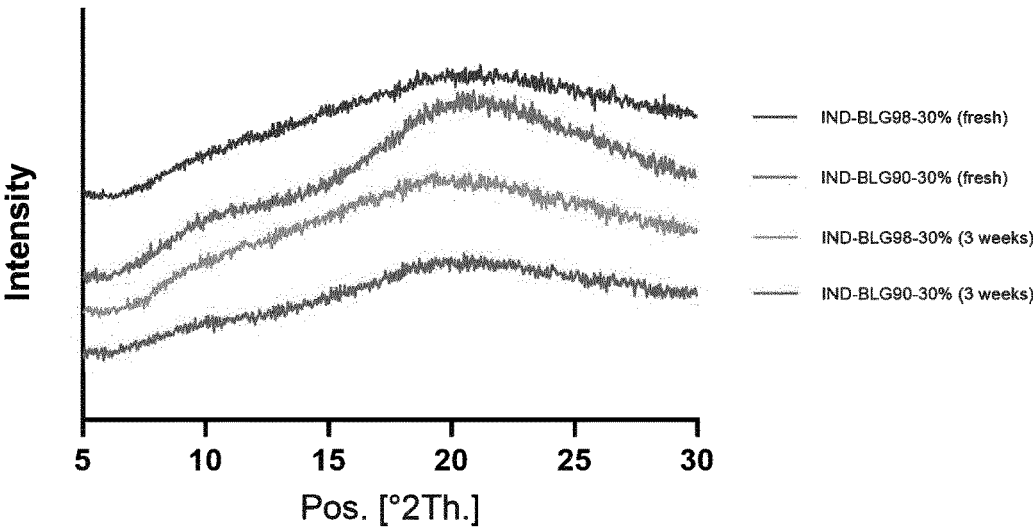
Figure 14:
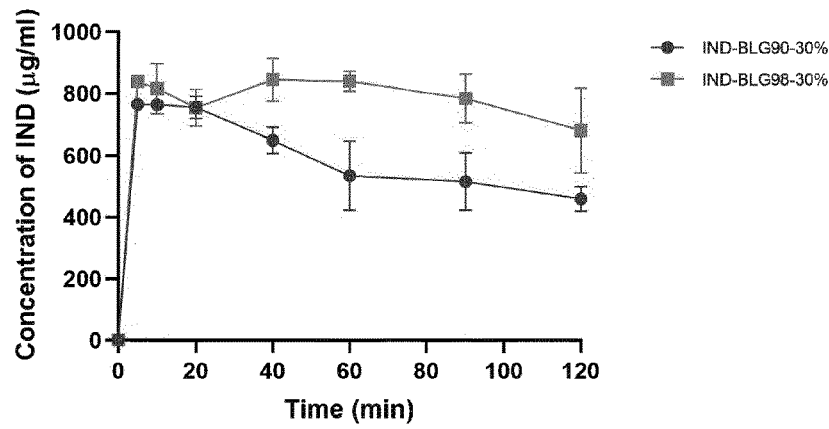
Figure 14:
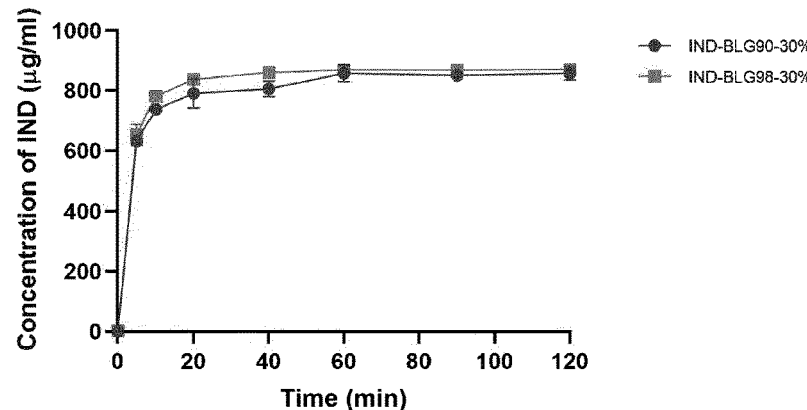

In order to test whether a lower drug loading could potentially improve drug release, co-amorphous formulations containing the Compound IND together with BLG98 or BLG90, at a drug loading of 30% (w/w) were prepared by ball milling. As shown in FIG. 13, the freshly prepared co-amorphous formulations at a drug loading of 30% (w/w) showed the appearance of an amorphous halo as well as single glass transition temperatures at Tg (IND-BLG98-30%)=141.0° C. and Tg (IND-BLG90-30%)=144.1° C., suggesting that both formulations resulted in single phase amorphous systems in combination with BLG98 and BLG90. At a Compound IND loading of 30% (w/w), the co-amorphous formulation containing BLG98 or BLG90, reached approx. 800 μg/ml drug release in both, 0.1M HCl and FaSSIF (FIG. 14). With respect to the dissolution medium 0.1M HCl, the dissolution was faster and much higher concentrations were obtained compared to the drug release of a co-amorphous formulation at a Compound IND drug loading of 50% (w/w) containing BLG98 (approx. 25 μg/ml, see FIG. 4). With respect to the dissolution medium FaSSIF, similar concentrations were obtained to a co-amorphous formulation at a Compound IND drug loading of 50% (w/w) containing BLG98 (FIG. 4). Hence, the results suggest that drug loadings below 50% (w/w) can increase the dissolution performance and solubility of the drug from the co-amorphous formulations with BLG.

Example 6—Powder Dissolution and Physical Stability of Co-Amorphous Formulation Obtained by Spray Drying (Drug RIF)

Figure 15:
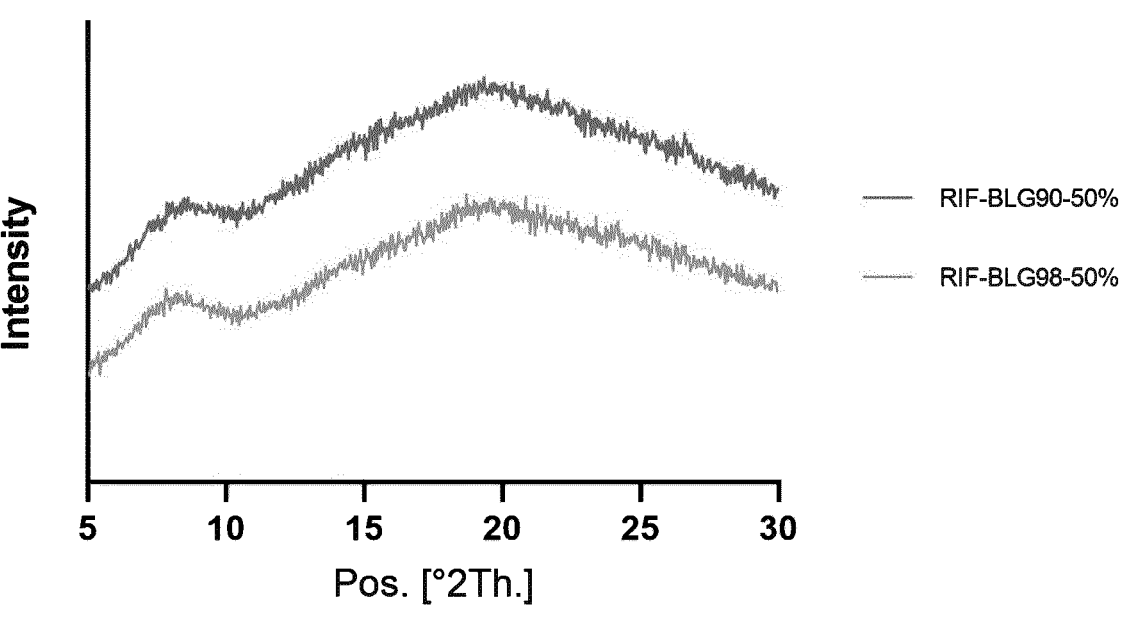
Figure 16:
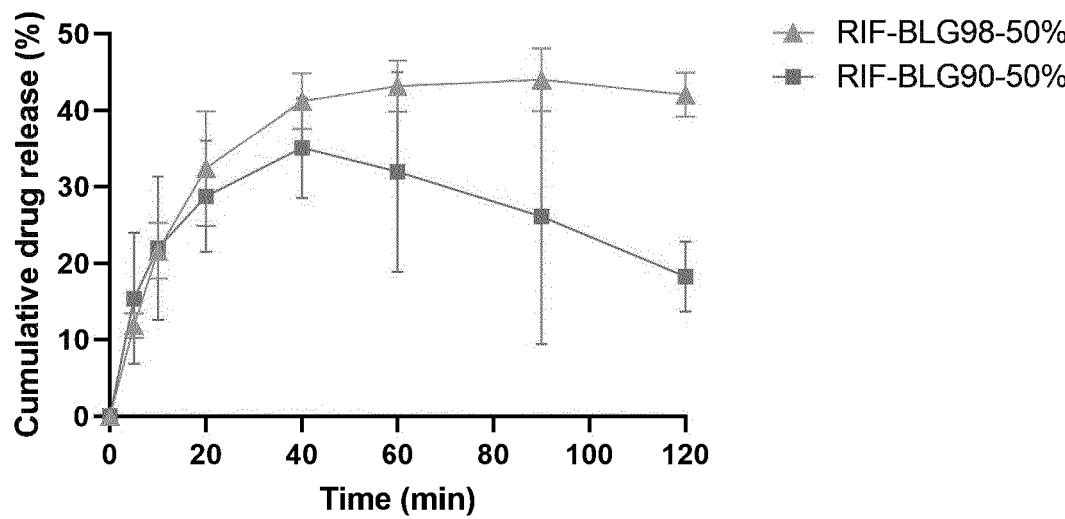

As shown in FIG. 15, the freshly prepared spray dried co-amorphous formulation containing RIF at a drug loading of 50% (w/w) showed the appearance of an amorphous halo as well as a single glass transition temperature at $T_{g(RIF-BLG98-50\%)}=198.4°$ C. and $T_{g(RIF-BLG90-50\%)}=199.2°$ C., suggesting that the obtained spray dried formulations resulted in single phase amorphous systems in combination with BLG98 and BLG90. With respect to the dissolution behavior (FIG. 16), the two spray-dried co-amorphous formulations showed a similar drug release in the first 20 min, however, post 20 min the co-amorphous formulation containing RIF together with BLG98 remained stable in the concentrations of dissolved RIF whereas the co-amorphous formulation containing the RIF together with BLG90 showed precipitation and hence was not able to maintain the drug in its supersaturated state. Furthermore, a higher drug release was obtained from the spray dried materials compared to the dissolution obtained from the ball milled co-amorphous formulations (FIG. 12).

The invention claimed is:

1. A co-amorphous form of an active pharmaceutical ingredient, a nutraceutical, or a veterinary medicinal product and beta-lactoglobulin, wherein the purity of the beta-lactoglobulin is at least 92% w/w of the total amount of protein comprised in the co-amorphous form.

2. The co-amorphous form according to claim 1, wherein the active pharmaceutical ingredient, nutraceutical, or veterinary medicinal product and beta-lactoglobulin has a solubility in water at 25° C. of less than 0.1 mg/ml.

3. The co-amorphous form according to claim 1, wherein the purity of the beta-lactoglobulin is at least 94% w/w of the total amount of protein comprised in the co-amorphous form.

4. The co-amorphous form according to claim 3, wherein the purity of the beta-lactoglobulin is at least 96% w/w of the total amount of protein comprised in the co-amorphous form.

5. The co-amorphous form according to claim 4, wherein the purity of the beta-lactoglobulin is at least 97% w/w of the total amount of protein comprised in the co-amorphous form.

6. The co-amorphous form according to claim 5, wherein the purity of the beta-lactoglobulin is at least 98% w/w of the total amount of protein comprised in the co-amorphous form.

7. The co-amorphous form according to claim 1, wherein the beta-lactoglobulin is bovine beta-lactoglobulin.

8. The co-amorphous form according to claim 1, wherein the co-amorphous form comprises from 5 to 85% w/w of the active pharmaceutical ingredient, nutraceutical, or veterinary medicinal product and from 15 to 95% w/w of the beta-lactoglobulin.

9. The co-amorphous form according to claim 1, wherein the co-amorphous form comprises from 5 to 35% w/w of the active pharmaceutical ingredient, nutraceutical, or veterinary medicinal product and from 65 to 95% w/w of the beta-lactoglobulin.

10. The co-amorphous form according to claim 1, wherein the active pharmaceutical ingredient, nutraceutical, or veterinary medicinal product has a solubility in water at 25° C. of less than 0.02 mg/ml.

11. A pharmaceutical composition comprising a co-amorphous form as defined in claim 1 and at least one pharmaceutically acceptable carrier or excipient.

12. The co-amorphous form according to claim 1, wherein the co-amorphous form comprises a nutraceutical and beta-lactoglobulin.

* * * * *